United States Patent [19]
Ishii

[11] 4,323,304
[45] Apr. 6, 1982

[54] DEVICE FOR FITTING AN ATTACHMENT TO AN ENDOSCOPE OCULAR SECTION

[75] Inventor: Fumiaki Ishii, Hachioji, Japan

[73] Assignee: Olympus Optical Co., Ltd., Tokyo, Japan

[21] Appl. No.: 215,755

[22] Filed: Dec. 12, 1980

[30] Foreign Application Priority Data

Dec. 24, 1979 [JP] Japan .................. 54-167775

[51] Int. Cl.³ .................. G03B 29/00; A61B 1/06
[52] U.S. Cl. .................. 354/62; 128/6
[58] Field of Search .................. 354/62, 63, 75, 76, 354/79, 80, 81; 128/4–6

[56] References Cited

U.S. PATENT DOCUMENTS

| | | | |
|---|---|---|---|
| 2,870,674 | 1/1959 | Mize | 354/79 X |
| 3,900,021 | 8/1975 | Makepeace et al. | 203/440 |
| 4,157,216 | 6/1979 | Plummer | 335/51 |
| 4,168,702 | 9/1979 | Ohshiro | 128/6 |
| 4,188,942 | 2/1980 | Fehlberg | 128/6 |

FOREIGN PATENT DOCUMENTS

| | | |
|---|---|---|
| 51-27677 | 4/1976 | Japan . |
| 54-65229 | 3/1979 | Japan . |
| 143572 | 4/1961 | U.S.S.R .................. 354/63 |

*Primary Examiner*—Donald A. Griffin
*Attorney, Agent, or Firm*—Frishauf, Holtz, Goodman and Woodward

[57] ABSTRACT

A device for fitting an attachment to an endoscope ocular section comprises a cylindrical receptacle which is set in the endoscope ocular section and has an end face, an adapter which is set on the ocular section attachment and fitted around the cylindrical receptacle by rotation, a coupling ring which is rotatably set in the adapter and has an end face capable of being pressed against the end face of the cylindrical receptacle, and connection mechanism for connecting the coupling ring and cylindrical receptacle together in a state prevented from being moved relative to each other. Provision of the connection mechanism prevents the end faces of the cylindrical receptacle and the coupling ring from sliding over each other, thereby eliminating the possibility that a coeliac observation is obstructed by the appearance of a gloss on the end face of the cylindrical receptacle due to its rubbing.

7 Claims, 4 Drawing Figures

DEVICE FOR FITTING AN ATTACHMENT TO AN ENDOSCOPE OCULAR SECTION

This invention relates to a device for fitting an endoscope ocular section with an attachment such as a photographic camera.

A photographic camera or any other attachment is generally fitted to an endoscope ocular section by a bayonet mechanism. In this case, the ocular section and attachment are relatively rotated for mutual engagement. The end face of the attachment slidably contacting the end face of the ocular section is undesirably rubbed to present a light reflective or glossy surface. Where, therefore, a coeliac cavity is observed by an endoscope in a room where an illumination source is set, the rubbed end face of the attachment shines, and light reflections therefrom enter the observer's eye, obstructing the proper observation of the coeliac cavity.

It is accordingly the object of this invention to provide an endoscope attachment-fitting device which suppresses the appearance of a gloss on the end face of the ocular section resulting from its rubbing when the endoscope attachment is fitted to the ocular section while being rotated, thereby ensuring a good coeliac observation.

An endoscope attachment-fitting device embodying this invention comprises a cylindrical receptacle which is formed in an endoscope ocular section and has an end face, a mount which is set on an ocular attachment and fitted around the cylindrical receptacle by relative rotation between the cylindrical receptacle and the mount, a coupling ring which is rotatably provided in the mount and whose end face is made to abut against the end face of the cylindrical receptacle, and means for connecting the coupling ring and cylindrical receptacle together in a relatively immovable state.

Provision of the coupling means prevents the end face of the cylindrical receptacle and that of the coupling ring from sliding over each other, thereby eliminating the appearance of a gloss on the end face of the cylindrical receptacle due to its rubbing against that of the coupling ring and the resultant obstruction of a coeliac observation.

This invention can be fully understood from the following detailed description with reference to the accompanying drawings, in which.

Figure 1:
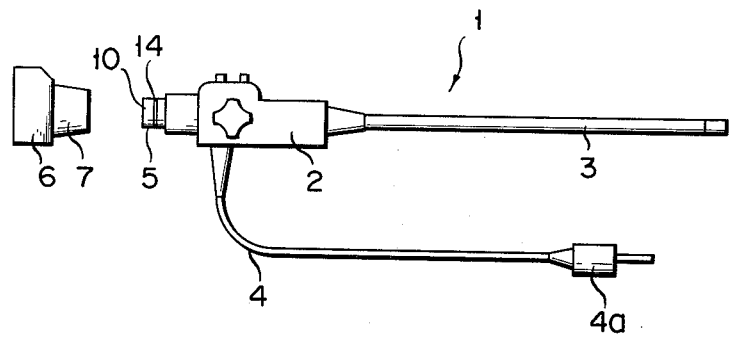
FIG. 1 shows an aligned arrangement of a front view of an endoscope and a lateral view of a photographic camera to be connected to the ocular section of the endoscope, the ocular section and the adapter of the camera being provided with an attachment-fitting device embodying this invention.
Figure 2:
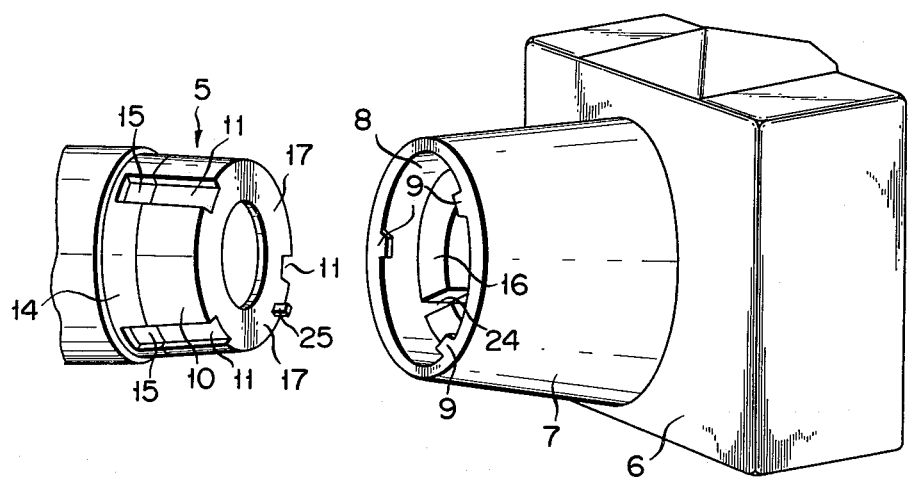
FIG. 2 is an exploded oblique view of an attachment-fitting device embodying this invention.

Referring to FIG. 1, an endoscope 1 comprises a substantially rectangular box-shaped control section 2, a tubular insertion section 3 projecting from one end of the control section 2, an umbilical cord or connection cord 4 which extends from one lateral wall of the control section 2 and whose free end is fitted with a connector 4a coupled to an external light source (not shown), and a cylindrical ocular section 5 connected to the other end of the control section 2. The distal end of the tubular insertion section 3 is provided with an observation window and an illumination window. The observation window is optically connected to the ocular section 5 by means of an image-transmitting optical system extending through the control section 2 and tubular insertion section 3. Through the illumination window is emitted an illumination light supplied from the external light source by means of an illumination optical guide extending through the control section 2, tubular insertion section 3 and umbilical cord 4. The other parts of the endoscope of this invention are constructed in the same way as those of the conventional endoscope, description thereof being omitted.

With the endoscope of the invention, a photographic camera 6, one of the ocular attachments, is detachably fitted to the ocular section 5 of the endoscope 1 by a bayonet mechanism. This arrangement is detailed below. A hollow cylindrical adapter 7 is formed on the front wall of the photographic camera 6. A plurality of bayonet pawls 9 radially project from the inner peripheral wall of the foremost edge portion of the distal end opening 8 equidistantly in the circumferential direction.

Provided at the distal end of the ocular section 5 is a bayonet ring 10 having an outer diameter substantially equal to the inner diameter of the adapter 7. Bayonet grooves 11 engageable with the bayonet pawls 9 are formed in the outer peripheral wall of the bayonet ring 10 equidistantly in the circumferential direction. Where the photographic camera 6 is fitted to the ocular section 5, the bayonet grooves 11 receive the corresponding bayonet pawls 9. In other words, the bayonet pawls 9 act as engagement members, and the bayonet ring 10 is used as a receptacle of the engagement members.

Figure 3:
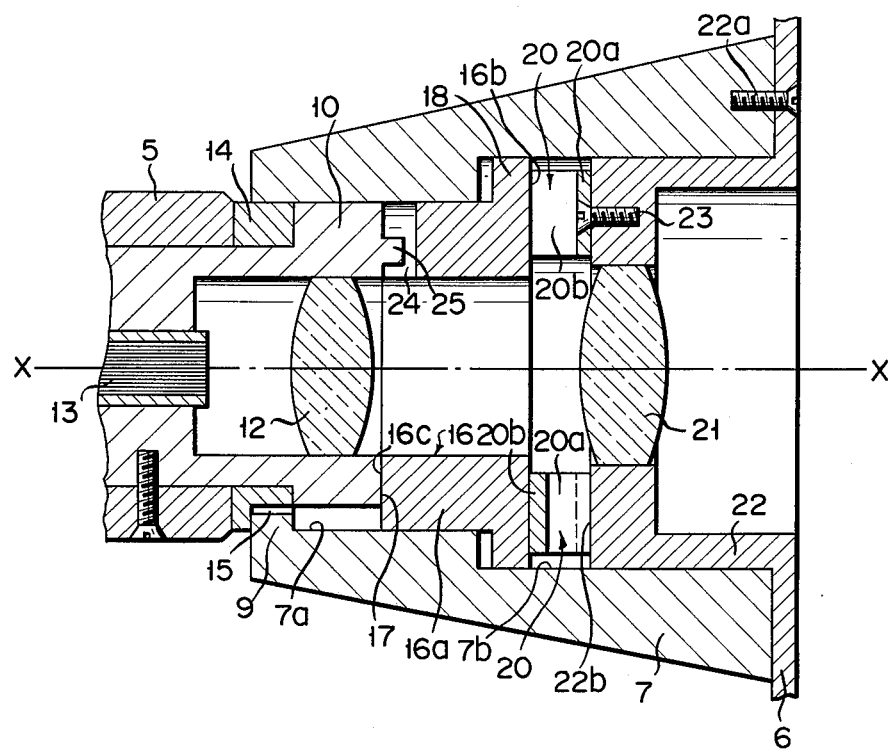
FIG. 3 is a longitudinal cross sectional view of FIG. 2.

As shown in FIG. 3, an ocular 12 is set so as to face the proximal end of an image guide 13 formed of an optical fiber bundle constituting part of the imagetransmitting optical system. An operation ring 14 is rotatably set on the outer periphery of the ocular section 5 close to the bayonet ring 10. Formed in the outer peripheral wall of the operation ring 14 are axially extending notches 15 corresponding to the bayonet grooves 11. Where the notches 15 are aligned with the corresponding grooves 11 by rotating the operation ring 14 in inserting the ocular section 5 into the adapter 7 of the photographic camera 6, the bayonet pawls 9 pass through the bayonet grooves 11 to be engaged with the corresponding notches 15. As a result, the bayonet ring 10 is securely fitted into the opening 8 of the adapter 7. Later when the adapter 7 is rotated, the operation ring 14 is turned in the same direction, causing the bayonet pawls 9 to be caught by the notches 15 and the inner end of the bayonet ring 10, and enabling the photographic camera 6 to be securely connected to the ocular section 5.

Reverting to FIG. 3, a smaller diameter cylindrical hole 7a is formed close to the forward end of the adapter 7. A larger diameter cylindrical hole 7b is formed close to the rear end of the adapter 7 concentrically with said smaller diameter cylindrical hole 7a. The cylindrical holes 7a, 7b are rendered coaxial with the optical axis X—X of the ocular 12. A coupling ring 16 comprises a hollow cylindrical body 16a slidably contacting the inner wall of the smaller diameter cylindrical hole 7a and a flange 18 formed concentrically with the hollow cylindrical body 16a at one end thereof and set in a larger diameter cylindrical hole 7b. A notch 24 is cut out in the front end portion of a hollow cylindrical body 16a. An engagement pin 25 axially projecting from the front end face or distal end face 17 of the bayonet ring 10 in the proximity of the outer periphery of the distal end face 17 of the bayonet ring 10 of the ocular section 5 is carried into the notch 24 when the bayonet ring 10 is inserted into the adapter 7. Insertion of the engagement pin 25 into the notch 24 prevents the coupling ring 16 from being rotated relative to the bayonet ring 10. The notch 24 and engagement pin 25 jointly constitute means for preventing the relative rotation of the bayonet ring 10 and coupling ring 16.

Securely inserted into the larger diameter cylindrical hole 7b of the adapter 7 is a hollow cylindrical lens mount 22 fixed to the front wall of the photographic camera 6 by set screws 22a. A space is provided between the front end face 22b of the lens mount 22 and the front end face 16b of the coupling ring 16, thereby allowing the coupling ring 16 to reciprocate axially of the adapter 7. Set in the lens mount 22 is an objective 21 which is rendered coaxial with an optical axis X—X of the ocular 12 when the photographic camera 6 is fitted to the ocular section 5.

In a space in the larger diameter cylindrical hole 7b, elastically urging means is provided between the front side 22b of the lens mount 22 and the corresponding front end face 16b of the coupling ring 16 normally to urge the coupling ring 16 toward the front end of the adapter 7. Where the adapter 7 is fitted to the ocular section 5, the rear end face 16c of the coupling ring 16 elastically abuts against the end face 17 of the ocular section 5 by the urging means, and clamps the bayonet ring 10 of the ocular section 5 between the coupling ring 16 and bayonet pawls 9.

Figure 4:
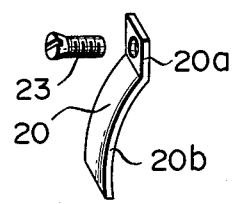
FIG. 4 is an oblique view of a plate spring used with the embodiment of FIGS. 1 and 2.

The above-mentioned urging means comprises, for example, a plurality of plate springs 20 shown in FIGS. 3 and 4. Each plate spring 20 comprises a base portion 20a securely set on the front end face 22b of the lens mount 22 in parallel therewith by a set screw 23 and an arm 20b which extends from the base portion 20a toward the front end face 16b of the coupling ring 16 in an outward convexed form and whose free end portion contacts the front end face 16b in parallel therewith. For example, three plate springs 20 are provided (only two are indicated in FIG. 3). They are equidistantly set in the circumferential direction of the front end face 22b of the lens mount 22 in such a manner that the arms 20b of the respective plate springs 20 are directed to the same circumferential sense, whereby the plate springs 20 axially urge the coupling ring 16 with an equal force.

Description is now given of the process of fitting the photographic camera 6 to the ocular section 5 of the endoscope 1. First, the bayonet pawls 9 of the adapter 7 are aligned with the bayonet grooves 11, and the bayonet ring 10 is inserted into the adapter 7. As a result, the bayonet pawls 9 pass through the bayonet grooves 11 and are engaged with the notches 15 of the operation ring 14. Later, the adapter 7 is rotated to effect the joint rotation of the bayonet pawls 9 and operation ring 14, thereby causing the bayonet pawls 9 to stop at the rear end of the bayonet ring 10. Where the ocular section 5 is going to be connected to the adapter 7, the rear end face 16c of the coupling ring 16 abuts against the distal end face 17 of the ocular section 5. Prior to said abutment, the engagement pin 25 of the ocular section 5 is engaged with the notch 24 of the coupling ring 16. Therefore, the coupling ring 16 and the ocular section 5 are assembled as if into a single body, thereby preventing the bayonet ring 10 and coupling ring 16 from being rotated relative to each other even when the adapter 7 is later rotated. In other words, when sliding on the side of the adapter 7, the coupling ring 16 does not rub the distal end face 17 of the ocular section 5. Thus, the distal end face 17 is not mirror polished.

Further, where the ocular section 5 is inserted into the adapter 7, the coupling ring 16 is pressed by the distal end face 17 of the ocular section 5, and is retracted against the urging force of the plate spring 20, thus remaining in a pressed state in tight contact with the end face 17 of the ocular section 5. Where the bayonet pawls 9 are stopped at the rear end of the bayonet ring 10 and the coupling ring 16 is pressed against the bayonet ring 10 when connection is effected between the ocular section 5 and coupling ring 16, the photographic camera 6 is securely supported by the ocular section 5.

The opposite process to that of fitting the photographic camera 6 to the ocular section 5 enables the adapter 7 to be released from the ocular section 5. In this case, too, the coupling ring 16 and ocular section 5 are engaged with each other, until the coupling ring 16 is removed from the end face 17 of the ocular section 5, thereby preventing the coupling ring 16 and ocular section 5 from being rotated relative to each other. The possibility is eliminated that the distal end face 17 of the ocular section 5 and the rear end face 16c of the coupling ring 16 are rubbed against each other.

Where, with an endoscope embodying this invention, an endoscope attachment is detachably fitted to the ocular section of the endoscope, it is possible to suppress the appearance of an unnecessary gloss on the end face of the ocular section due to its rubbing. In other words, even where an endoscope is applied, for example, in a room where an illumination source is set, the front end face of the ocular section fitted with a photographic camera does not shine at all, thereby eliminating the obstruction of a coeliac observation.

With the foregoing embodiment, a photographic camera was used as an attachment to the ocular section of the endoscope. However, this invention is obviously applicable to the case when any other attachment (for example, a teaching scope) is fitted to the ocular section of the endoscope.

What is claimed is:

1. A device for fitting an ocular section attachment to an ocular section of an endoscope which comprises:
    a cylindrical receptacle which has a first end face and is provided on an endoscope ocular section;
    an adapter which is provided on an ocular section attachment to be fitted around the cylindrical receptacle by being rotated;
    a coupling ring rotatably disposed in the adapter and having a second end face abuttable against the first end face of the receptacle; and
    connection means for connecting the coupling ring and cylindrical receptacle together in a state preventing their relative movement.

2. The attachment-fitting device according to claim 1, wherein said connection means comprises an engagement pin projecting from the first end face axially of the cylindrical receptacle and a notch cut out in the second end face of the coupling ring in alignment with the engagement pin.

3. The attachment-fitting device according to claim 2, which further comprises urging means for elastically urging the cylindrical receptacle toward the second end face.

4. The attachment-fitting device according to claim 3, wherein the urging means comprises plate springs.

5. The attachment-fitting device according to claim 3, wherein said adapter comprises a first cylindrical hole whose diameter is substantially equal to that of the cylindrical receptacle and a second cylindrical hole which is disposed deeper than the first cylindrical hole and is formed concentrically with the first cylindrical hole, said second cylindrical hole having a large diameter than the first cylindrical hole; and said coupling ring has an outer diameter substantially equal to the inner diameter of the first cylindrical hole, and comprises a cylindrical body insertable into the first cylindrical hole and a flange which is mounted on said cylindrical body to be set in the second cylindrical hole.

6. The attachment-fitting device according to claim 5, wherein said urging means comprises plate springs.

7. The attachment-fitting device according to claim 1, wherein said ocular section attachment is a photographic camera.

* * * * *